United States Patent [19]
Seiden et al.

[11] Patent Number: 5,220,513
[45] Date of Patent: Jun. 15, 1993

[54] GAS CONTENT MEASUREMENT IN A SEALED CONTAINER OF LIQUID BY DEGASSING

[76] Inventors: Louis W. Seiden, 11100 Rosemont Dr., North Bethesda, Md. 20582; Marc J. Epstein, 322 Riverview St., Florence, N.J. 08518

[21] Appl. No.: 656,713

[22] Filed: Feb. 19, 1991

[51] Int. Cl.$^5$ .................. G06F 15/46; G01L 7/00
[52] U.S. Cl. .................. 364/500; 364/499; 364/571.05; 73/19.06; 73/19.01
[58] Field of Search .............. 364/496, 497, 500, 558, 364/571.01-571.08, 499; 73/19.01, 19.06, 24.42

[56] References Cited

U.S. PATENT DOCUMENTS

| | | | |
|---|---|---|---|
| 4,153,837 | 5/1979 | Ross | 250/343 |
| 4,179,918 | 12/1979 | Van Strien | 73/19.06 |
| 4,423,739 | 1/1984 | Passaro et al. | 250/345 X |
| 4,457,808 | 7/1984 | Taylor et al. | 364/571.05 X |
| 4,578,762 | 3/1986 | Wong | 364/497 |
| 4,607,342 | 8/1986 | Seiden et al. | 364/500 X |
| 4,674,061 | 6/1987 | Diskowski et al. | 364/558 X |
| 4,731,732 | 3/1988 | Warchol et al. | 364/497 X |
| 4,745,794 | 5/1988 | Steichen et al. | 73/19.06 X |
| 4,766,550 | 8/1988 | Byers et al. | 364/497 |
| 4,926,681 | 5/1990 | Fitzpatrick | 73/19.06 X |
| 5,029,103 | 7/1991 | Corbett | 73/19.06 X |

*Primary Examiner*—Kevin J. Teska

[57] ABSTRACT

The current generally accepted method for measuring the air content in a beverage liquid (usually carbonated) is by a non-electronic chemical technique. This invention measures the oxygen component of a beverage gas using a polarographic probe, ultrasonic degassing, a special valving technique, and microprocessor based software. The measurement is made in the gaseous state in a two chamber (measurement and foam) system. The device is controlled by an electronic console that is built around a microprocessor which sequences and times the valves, receives data from the oxygen probe and its accompanying temperature compensation circuit, and displays the data. The sensitivity of the oxygen probe and the foaming nature of the beverage dictate the size of the chambers. The test generally must be done in several passes since all the measurable gas usually cannot be concentrated in the measure chamber in one pass. An alternative method would use several chambers and one pass. In addition, this device has an interface piercing head manifold that allows $CO_2$ and oxygen to be tested in the same container and in one operation.

18 Claims, 6 Drawing Sheets

GAS CONTENT MEASUREMENT IN A SEALED CONTAINER OF LIQUID BY DEGASSING

BACKGROUND OF THE INVENTION

Air content—via the oxygen component of air—in a liquid is a quantity that is of interest to the canning industry in general and the beverage industry in particular. This invention utilizes a polarographic probe to make an electronic measurement of the oxygen component in the gaseous state. Although it might be theoretically possible to make a measurement in the liquid, such a measurement is both difficult mechanically and difficult to analyze. The interpretation of the data because of solubility problems which are a function of additives (wanted and unwanted) would be very complex and troublesome. Temperature and pressure variations are also a problem. Air is primarily nitrogen and oxygen in approximately a 4 to 1 ratio (80% nitrogen, 20% oxygen). There is no direct electronic measurement for nitrogen but air content can be calculated by measuring the oxygen component. Also this measurement can separate the amount of air in the head space of a drink (that space that is not occupied by liquid) from the air in the beverage.

TECHNICAL FIELD

A direct comparison can be made; that is, the ratio of air in the test mode to air in the calibration mode is the same as the ratio of oxygen in the test mode to oxygen in the calibration mode.

$$\frac{\text{AIR test}}{\text{AIR calibration}} = \frac{\text{OXYGEN test}}{\text{OXYGEN calibration}}$$

In a carbonated beverage there are primarily two forms of gas present. The desired gas is $CO_2$ and the undesirable gas is air. (A description of $CO_2$ measurement can be found in U.S. Pat. No. 4,607,342—Apparatus for Remotely Measuring and Controlling the Carbon Dioxide in a Beverage Liquid: On-Line). This invention measures the air content in the beverage which is ideally zero. There are several technologies employed to accomplish this measurement.

1. The polarographic probe measures oxygen through a physical chemical process that converts oxygen to an electronic signal. The general equations are:
At the gold cathode:

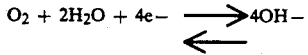

At the silver anode:

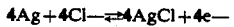

$CO_2$ is not an interferent for the polarographic probe.

2. Ultrasonics is a conventional and convenient method of degassing a liquid. Air is less soluble than $CO_2$. The overwhelming amount of $CO_2$ in the liquid pushes the small amount of air out of the liquid and the head space and eventually into a test chamber above.

3. A microprocessor device provides control of the calibration and measuring sequences.

SUMMARY OF THE INVENTION

The conventional method for measuring the air content in a carbonated beverage is a chemical test using a hydroxide solution. The hydroxide solution is used to absorb $CO_2$ and while a 10% solution will work, a stronger solution will function more rapidly and is less quickly diluted by beer which works up the Burrette. After the test is finished, the valve assembly should be thoroughly flushed with water to remove the sample (1). The purpose of this invention is to measure the air content in a carbonated beverage so that the test has the following advantages:

1. The test requires no dangerous chemicals.
2. The test is electronic.
3. The test is automatic so that no operator is required after the test is started.

Oxygen can be measured with a Clark or polarographic type cell (2) or by a Mancy or galvanic type cell (3). Dissolved oxygen in a liquid normally is measured in the liquid state by such a probe. This invention removes the gas from the beverage (using ultrasonics or other mechanical means for degassing), deals with the special problems due to foaming, and provides an accurate calibration method and a repeatable result in close agreement with chemical tests.

(1) Zahm Practical Testing Instruments 15th Edition, pages 12 and 13
(2) L. C. Clark J. Appl. Physiol., 6 189 (1953)
(3) K. H. Mancy, D. A. Okun, and C. N. Reilley J. Electroanal. Chem., 4, 65 (1962)

DESCRIPTION OF THE DEVICE

Figure 1:
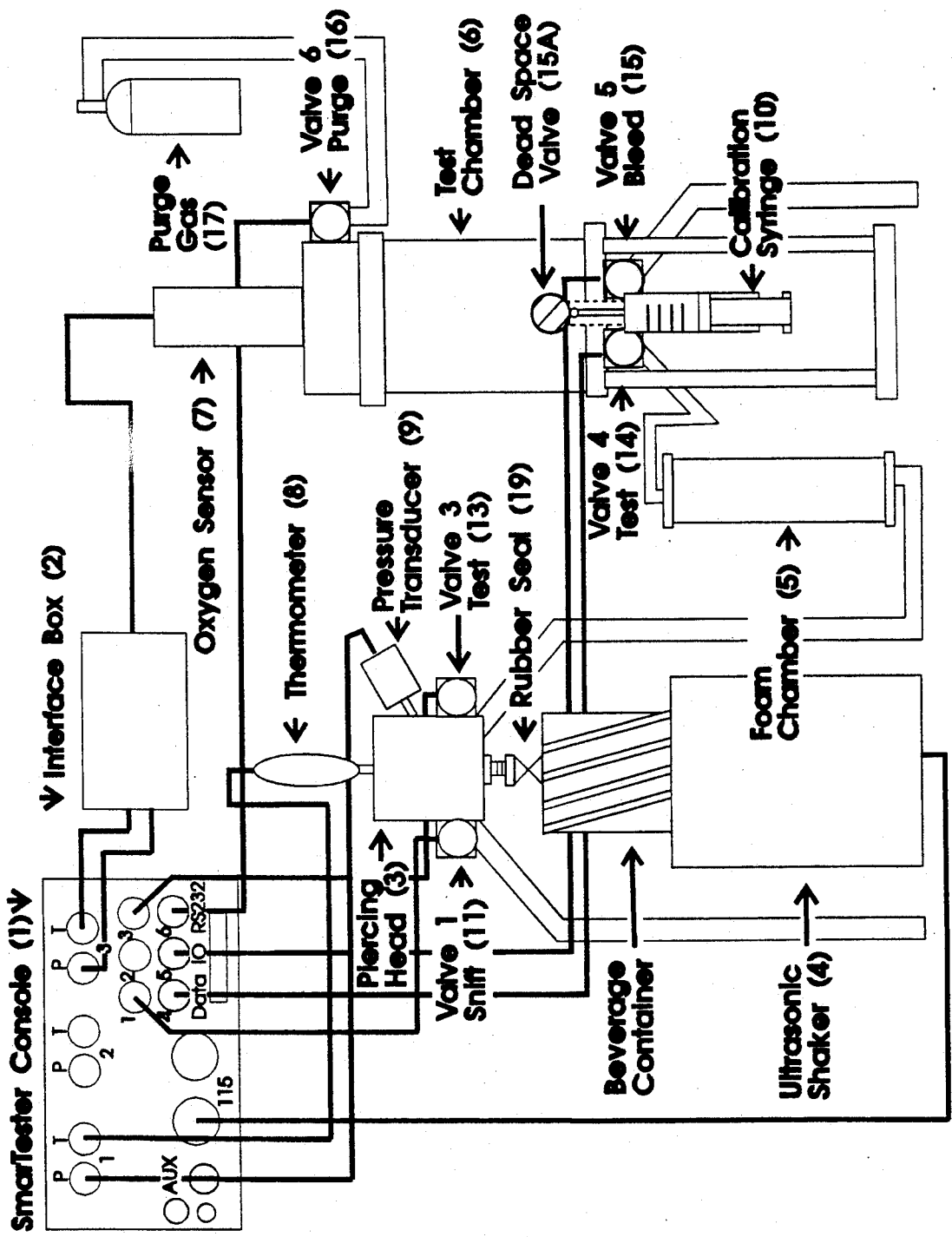
FIG. 1—A block diagram of the system for the measurement of air in a beverage liquid, including electrical and mechanical connections for air content test and a piercing head manifold.
Figure 2:
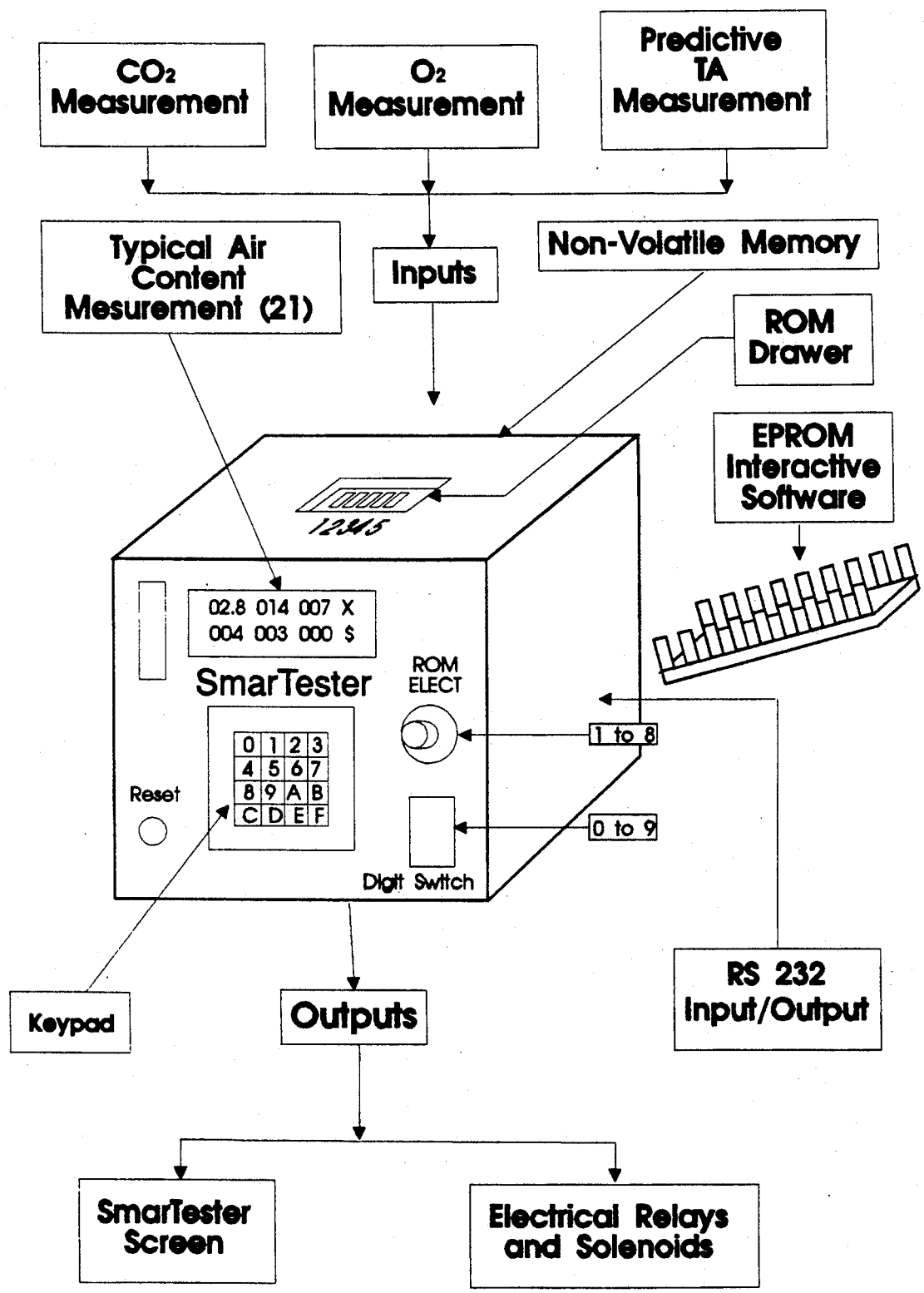
FIG. 2—A console that controls solenoid valves and allows for an oxygen measurement with display of partial oxygen measurements and their sum.

An apparatus to measure the air content in a beverage liquid is diagramed in FIG. 1. The measurement is accomplished in two modes—the calibration mode and the test mode. This test can be achieved independently or in conjunction with a $CO_2$ test. All electrical connections are at the rear of the console (1). These connections are the control points for valves, ultrasonic devices, RS-232 communications, and electronic measuring probes-temperature (8), pressure (9), oxygen (7).

The calibration mode:

The most accurate method of calibrating any device is in the vicinity of the test result. The calibration syringe (10) can be opened to one of two positions (atmosphere and a test chamber) (6). The system (the test chamber, a foam chamber (5), and the associated valves and tubes) is purged of air with a purge gas (17)—generally $N_2$ or $CO_2$. When the system is purged, the console saves and records the low end of the range. A calibration syringe (10) is open to atmosphere and pulled back to the required calibration point (usually 10 cc). The calibration syringe is then put into the second position via a mechanical dead space valve (15A); the syringe is depressed and the 10 cc's of air are now in the test chamber. At this point the high end range is measured, saved, and recorded.

Figure 4:
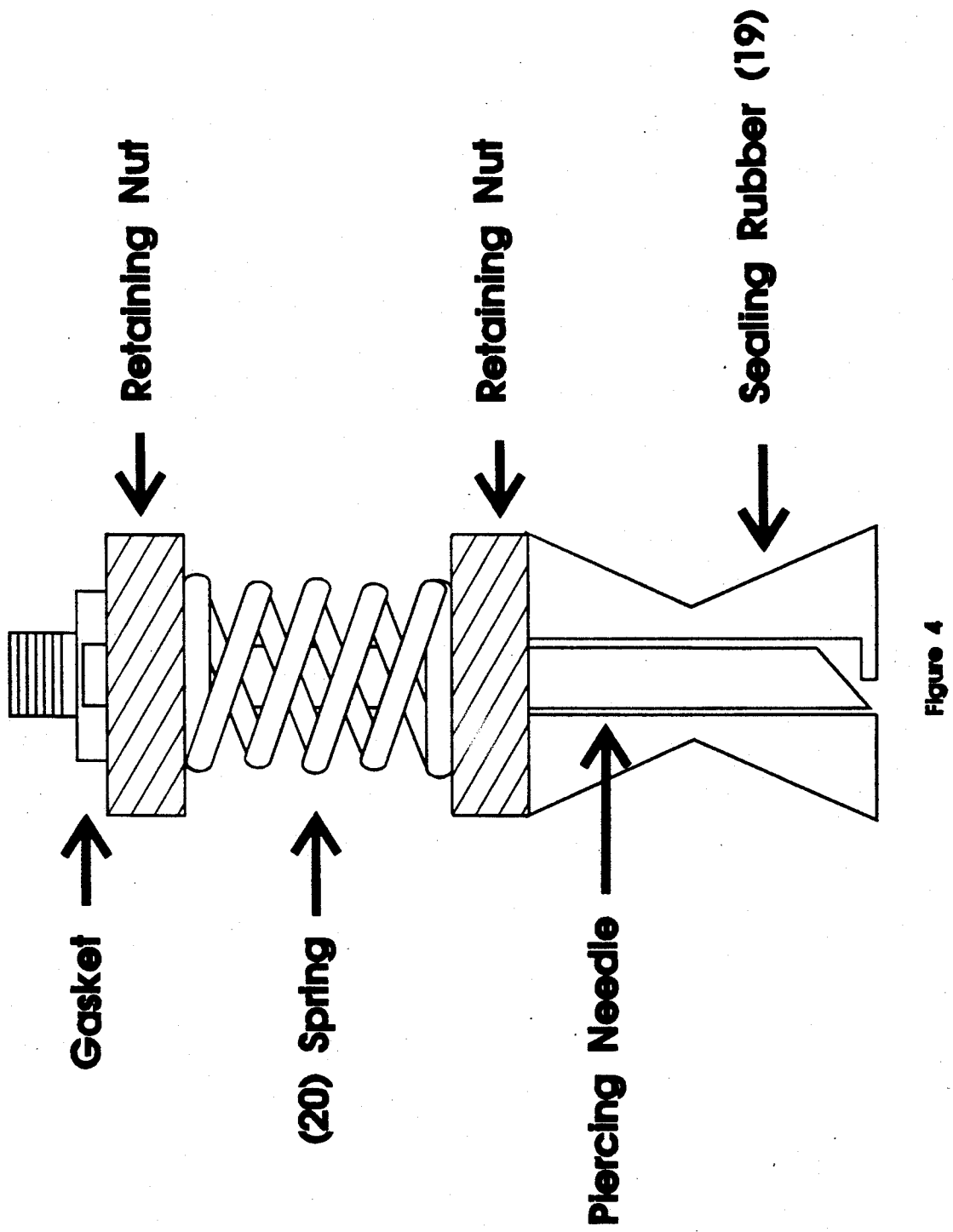
FIG. 4—A detailed view of a retractable spring-loaded piercing needle.
Figure 5:
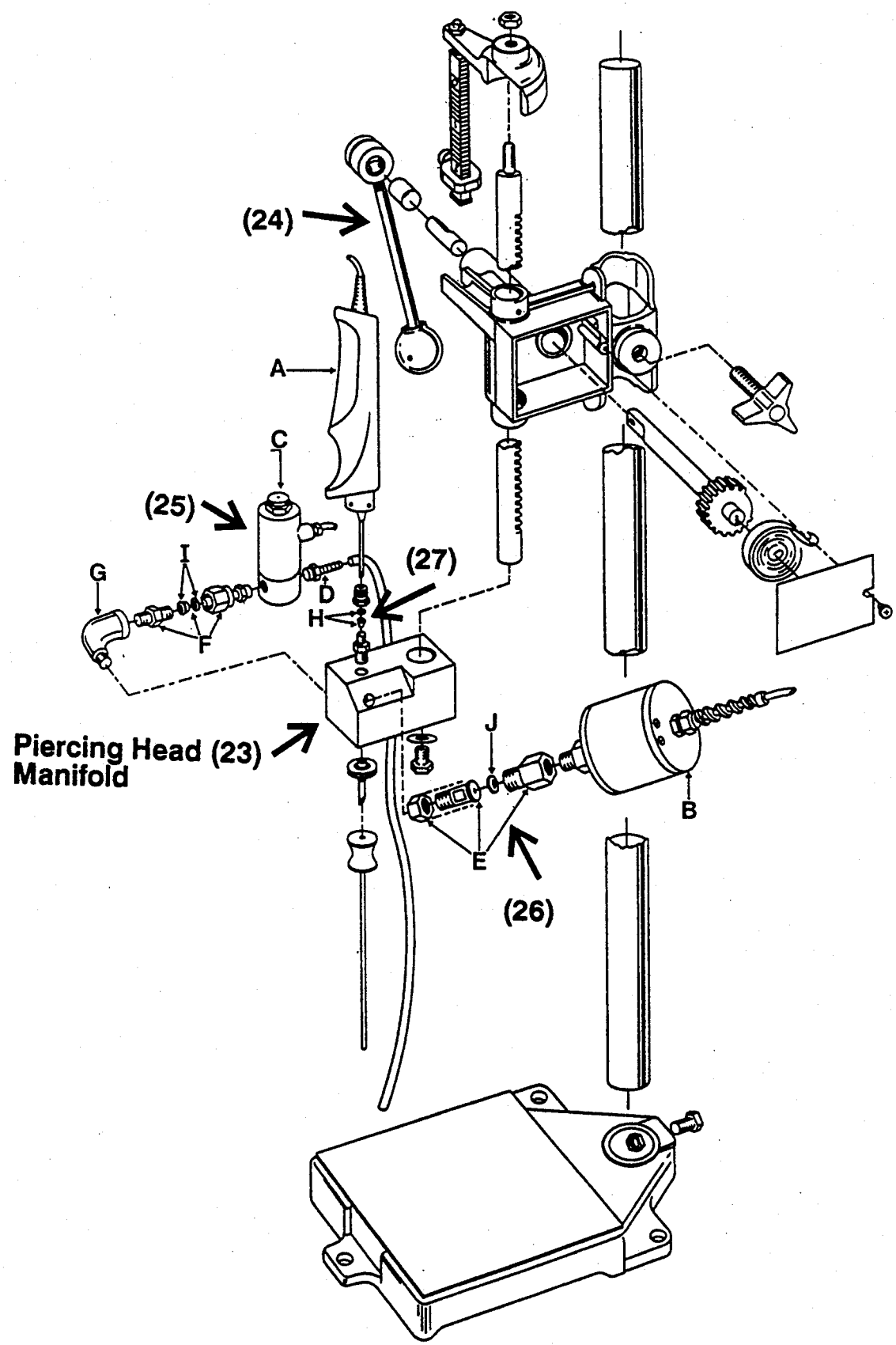
FIG. 5—Piercing head manifold attached to device that applies a positive downward pressure.
Figure 6:
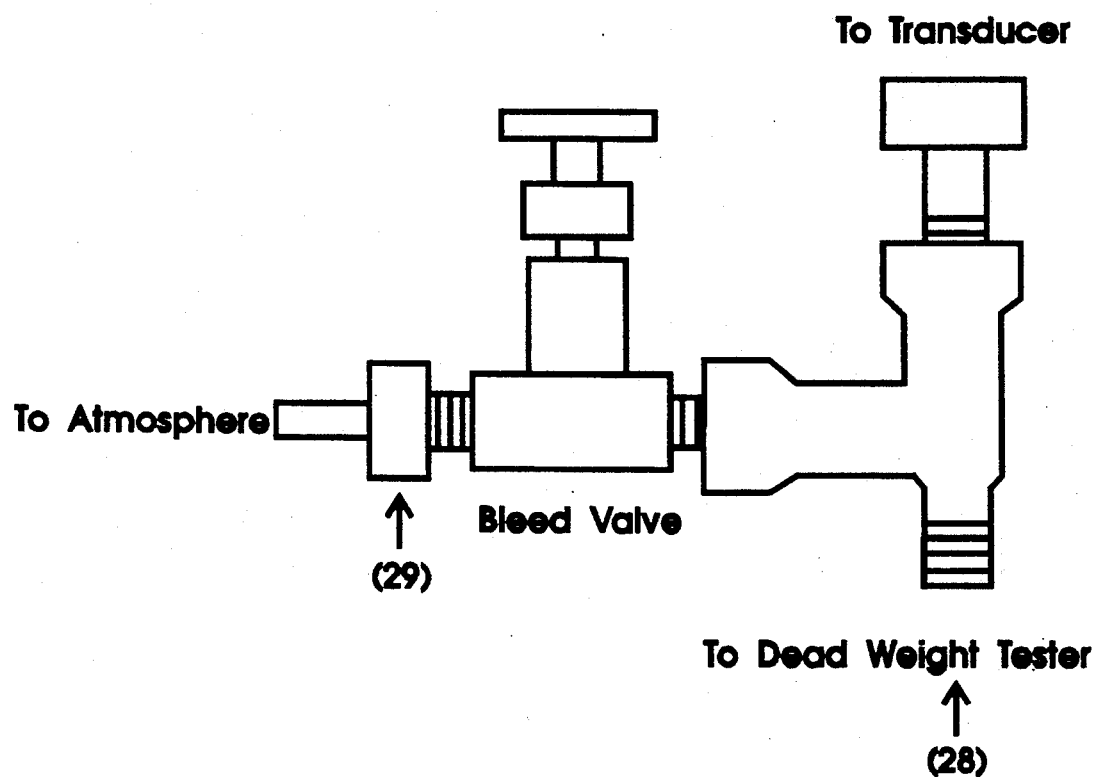
FIG. 6—Special fitting for dead weight tester.

The test mode:

A beverage container (18) that is to be measured for air content is pierced by a hollow needle (under a rubber seal (19) see FIGS. 1, 4 and 5) attached to a piercing device which applies a positive downward pressure. The piercing head manifold (23) in FIG. 5 is attached to a spring loaded device (24) that applies a permanent downward pressure and in turn holds the piercing needle and seal in place after the container is punctured. The manifold contains various internal pathways that allow the beverage gases and liquids to find their way to the proper part of the system. There is either one or two remotely or manually operated valves (25) that allow beverage gas to flow to the air content test or to be bled into the atmosphere. The pressure device is attached to the piercing head manifold by a special connector (26) in FIG. 5. Another special connector (28) (see FIG. 6) with the same type of fitting (29) attaches to a dead weight tester. These fittings allow the pressure transducer to be easily removed from the manifold, to be easily attached to the dead weight tester, and opened to atmosphere for low end ranging. Also an electronic thermometer is attached to the manifold with a special seal (27). To prevent premature piercing of the container, a spring (20) is set above the sealing rubber so the rubber can be set on top of the beverage container without piercing the container. Piercing occurs when the positive downward pressure is applied. The piercing head manifold which internally connects a thermometer (8), a pressure transducer (9), a snift or bleed valve (11), and a test valve (3) that allows the gas to flow to the foam chamber and the air test chamber. An ultrasonic device (4) is turned on for a finite time (3 to 10 sec.) and then off. (This cycle is repeated 3 to 5 times since all the air cannot be moved into the test chamber in one cycle because of the pressure and volume build up when degassing-an alternative would be several chambers and one pass.) This is a two part measurement; the first part of which is the zero or low end of the measurement; the second part is the raw measurement. The measurement in each cycle is the difference of the two.

MEASUREMENT (test gas) per cycle=RAW MEASUREMENT−ZERO MEASUREMENT

Figure 3:
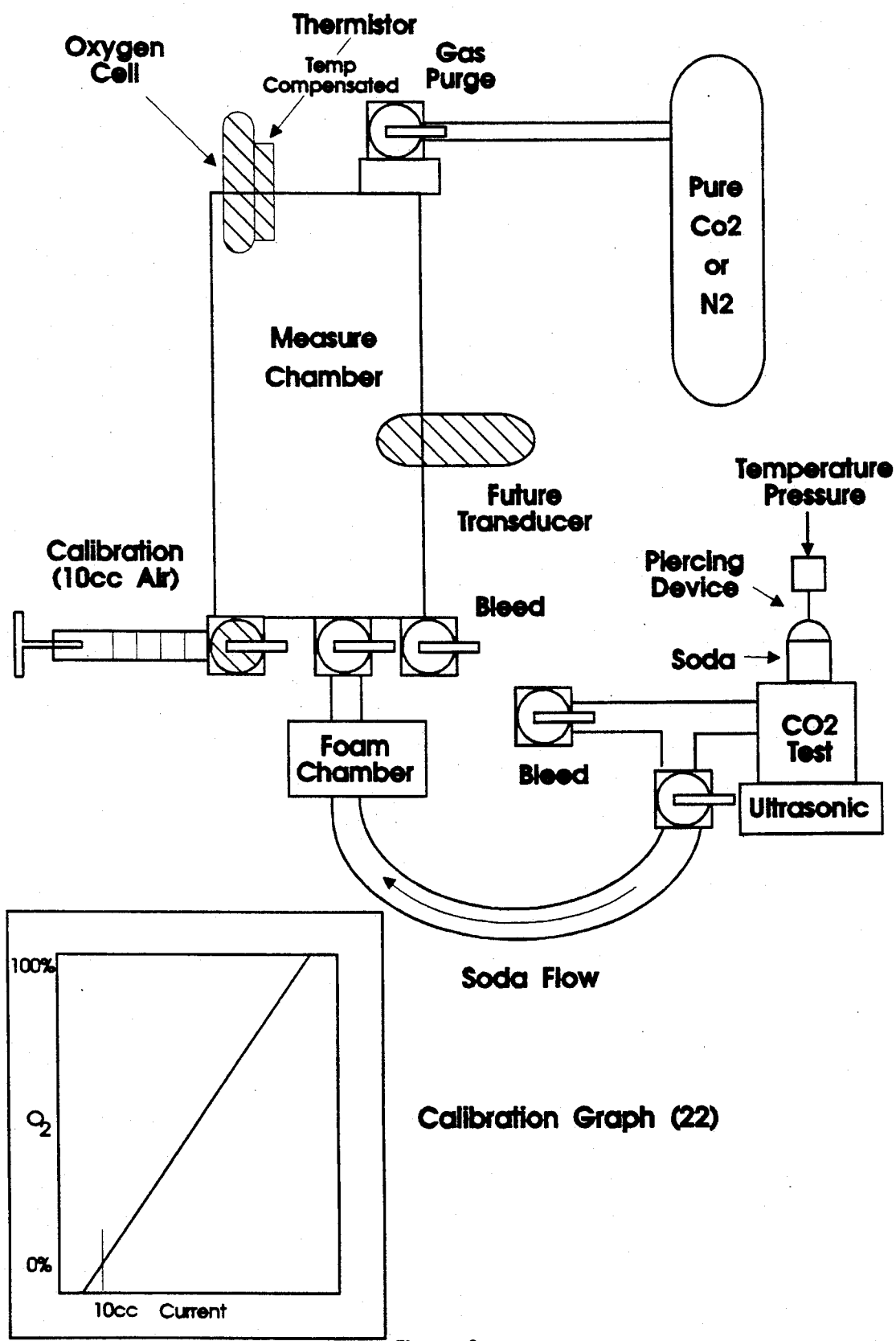
FIG. 3—A pictorial summary of the system with a graph that shows a calibration point.

Pressure build up is bled off at valve 5 (15) in preparation for the next cycle. The test chamber is a fixed volume cylinder and must remain so for the calibration to hold. A major difficulty arises from the fact that carbonated drinks foam when agitated (beer being generally worse than soft drinks). The foam chamber is placed between the beverage container and the test chamber to absorb the foam. If the foam or a portion of the liquid gets into the test chamber then its volume is decreased and the membrane at the tip of the oxygen probe can get wet. Both of these occurrences can affect the final result and must be avoided. The size of the test chamber, the size of the foam chamber, and the sensitivity of the oxygen probe (set at an interface box(2)) are all interrelated and are experimentally optimized. In the optimized situation 3 to 5 passes are required to get all of the air (normally 80% to 100% in 3 passes). The limitations are the pressure that the test chamber will reach and the pressure the oxygen probe will tolerate. A transducer will monitor this pressure; the pressure will tend to zero as the test is completed. FIG. (2) shows the console and a display of the air content data. The data on the screen (21) indicates that there are 2.8 cc of air in the sample in 5 cycles or passes (2.8=1.4+0.7+0.4+0.3+0.0—Note missing decimal point in the partial results). FIG. 3 is a pictorial summary of the system. The graph (22) shows that the calibration is accomplished near the test point.

We claim:

1. A method for measuring an amount of a gas in a sealed container of fluid comprising the steps of:
   a. piercing the sealed container with a piercing mechanism,
   b. degassing the pierced container to release the gas,
   c. passing the released gas into a test chamber, and
   d. measuring the amount of a component of the released gas in the test chamber with a gas specific sensor.

2. The method of claim 1 wherein the released gas is passed through a foam chamber before entering the test chamber, wherein the foam chamber is attached in between the test chamber and the pierced container to hold unwanted liquid and maintain the fixed volume of the test chamber.

3. The method of claim 1 wherein the released gas measured is carbon dioxide.

4. The method of claim 1 wherein the released gas measured is nitrogen.

5. The method of claim 1 wherein the released gas measured is oxygen.

6. The method of claim 1 wherein the amounts of two or more released gasses in the same container are measured.

7. The method of claim 1 wherein the amount of the released gas in each of a series of containers is measured.

8. The method of claim 1 wherein the amount of the released gas is determined after the completion of at least two cycles of steps.

9. The method of claim 1 which further comprises a calibration step, performed prior to piercing the sealed container wherein:
   a. the gas specific sensor produces a first output signal in the absence or at a low level of said gas,
   b. a measured amount of said gas is injected into the test chamber,
   c. the gas specific sensor produces a second output signal in the presence of the measured amount of said gas, and
   d. said measurement is calibrated as a function of the first output signal and the second output signal.

10. A device for measuring an amount of a gas in a sealed container of fluid comprised of:
    a. a piercing mechanism for piercing the sealed container,
    b. a degassing mechanism connected to the piercing mechanism for releasing the gas from the pierced container,
    c. a test chamber which receives the released gas, and
    d. a gas specific sensor which measures the amount of a component of the released gas.

11. The device of claim 10 which further comprises a foam chamber, which is attached in between the test chamber and the pierced container to hold unwanted liquid and maintain the fixed volume of the test chamber.

12. The device of claim 10 which further comprises a calibration mechanism coupled to the test chamber.

13. The device of claim 10 wherein the piercing mechanism is a manifold comprised of a retractable piercing needle.

14. The device of claim 10 wherein the degassing mechanism is selected from a group which consists of an ultrasonic degassing mechanism, a mechanical degassing mechanism, a degassing mechanism which utilizes an external driving gas, and a degassing mechanism which utilizes an internal driving gas.

15. The device of claim 10 further comprising a computer connected to the piercing mechanism, the degassing mechanism, the test chamber, and the gas specific sensor to automatically measure the amount of the gas in each of a series of sealed containers.

16. The device of claim 10 which comprises two or more test chambers.

17. The device of claim 10 wherein the gas specific sensor is a carbon dioxide sensor, a nitrogen sensor, or an oxygen sensor.

18. The device of claim 10 which comprises two or more gas specific sensors.

* * * * *